United States Patent [19]

Redaelli

[11] 4,313,880

[45] Feb. 2, 1982

[54] EXTRACTIVE PROCESS FOR PREPARING APIGENIN

[75] Inventor: Claudio Redaelli, Missaglia, Italy

[73] Assignee: Benomelli S.p.A., Dolzago, Italy

[21] Appl. No.: 87,932

[22] Filed: Nov. 27, 1979

[30] Foreign Application Priority Data

Oct. 25, 1978 [IT] Italy .............................. 29099 A/78

[51] Int. Cl.³ .......................................... C07D 311/30
[52] U.S. Cl. ..................................... 260/345.2; 536/8
[58] Field of Search ......................... 260/345.2; 536/8

[56] References Cited

U.S. PATENT DOCUMENTS 2,359,126  9/1944  Lautenschläger et al. ............. 536/8

Primary Examiner—Nicky Chan
Attorney, Agent, or Firm—Morgan, Finnegan, Pine, Foley & Lee

[57] ABSTRACT

The invention concerns a process for producing apigenin, wherein it is extracted with a water/ethanol mixture from ligules of Matricaria Chamomilla L. and after purified by crystallization from ethanol.

Concerned is also the use of the pure product apigenin in human spasmolytic therapy.

2 Claims, No Drawings

EXTRACTIVE PROCESS FOR PREPARING APIGENIN

This invention relates to a new industrially significant extractive process for producing apigenin, and to therapeutic compositions of spasmolytic activity containing apigenin as their active principle. Apigenin is the name given to 4′,5,7-trihydroxyflavone of formula

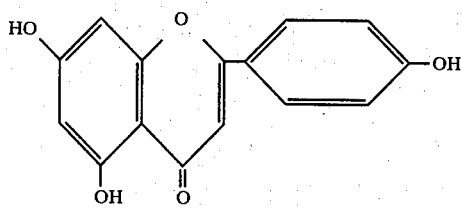

which has been known to botanists for many years, firstly identified in the form of glucoside (apiin) in parsley extracts, and then in the total extracts of camomile flowers, again in the form of various glucosides not completely identified, and as aglicone.

Studies conducted up to the present time on apigenin have been of a strictly scientific kind, in that the possibility of economically using the natural raw materials which contain it for its large-scale production has never been conceived.

In particular, the inflorescence, improperly known as flowers, of the Matricaria Chamomilla, which have been the only parts of the plant used up to the present time for industrially preparing total extracts, contain apigenin in a percentage not exceeding 0.2-0.3 on the dry basis, and in mixture with other flavones having strictly analogous physical properties, because of which it is very difficult to separate it.

Under such conditions, an economically convenient industrial process for the extractive production of apigenin from camomile flowers is inconceivable.

An extractive process, which forms the object of the present invention, has now been discovered which is extremely simple and economical, because of the nature of the solvents used, the number of extractive stages and the total processing time. This process uses as its raw material not the camomile inflorescence but instead the ligules of Matricaria Chamomilla L., which represent a part of the plant which up to the present time has been discarded and for which there has been no known industrial use.

The new process comprises essentially the following operational stages:

(a) totally extracting the ligules in a continuous extractor for a time of 7-8 hours, with a water/ethyl alcohol mixture containing at least 30% by volume of ethyl alcohol;

(b) evaporating the extract to dryness then again taking it up in ethyl ether in the proportion of about 10 parts by volume per 1 part by weight of the initial ligules, then leaving it under strong agitation for 24 hours and filtering;

(c) hydrolysing the solid obtained by treating it with a volume of 10% HCl approximately equal to the volume of ether used in stage (b). In this manner, after about 10 hours, all the kpigenin extracted from the ligules both as such and in the form of glucosides precipitates in known manner as free aglicone. The apigenin can be further purified by crystallisation from ethanol or from other suitable solvents.

With the process of the present invention, a pure apigenin yield of 4.5-6% with respect to the initial ligules in their dry state is obtained. Such a yield is to be considered truly interesting from the point of view of industrialisation of the process, especially so because of the very low commercial value of the material processed.

The great advantage of using Matricaria Chamomilla L. ligules as the starting material derives not only from the fact that the ligules contain 7-9% of apigenin in the form of glucosides and 0.3-0.5% free apigenin (and therefore approximately 10% of useful product for the purposes of the present process), but also, and in particular, the fact that apigenin is the only flavone present in the ligules, and there are therefore no separation problems. The other substances present in the ligules are so different in their chemical nature from the flavones that it has been possible, both in the initial extractive stage and in the subsequent separation stage, to find extremely selective operational conditions which enable practically all the apigenin to be recovered in the pure state.

It should be noted that the operational conditions (a), (b), (c) indicated heretofore are the optimum conditions which critically give maximum selectivity, and thus the maximum yield of the product of pharmaceutical purity, with industrially valid process times and materials.

Many other solvents and solvent mixtures have been tried, but in no case have the results been totally satisfactory from the industrial process aspect, whereas they could still be considered acceptable for preparing small quantities of product for laboratory study purposes.

In stage (a), it has for example been found that the use of water/ethanol mixtures with an ethanol content of progressively less than 30% by volume leads to increasingly incomplete extraction of the free apigenin contained in the ligules, down to the point where there is total insolubility and thus practically total loss of the free aglicone when water alone is used as the extraction medium.

If water/ethanol mixtures of increasing ethanol content are used, there is no substantial variation in the results, while obviously the economic convenience decreases proportionally with the quantity of alcohol used, until the process becomes decidedly uneconomical with absolute ethanol.

Common organic solvents such as acetone and ethyl acetate have on the other hand shown a decidedly poor extractive power towards the apigenin glucosides.

In stage (b) in which it was necessary to find a solvent in which the apigenin glucosides and aglicone are both practically insoluble whereas the many organic substances extracted in the first total extraction stage are totally soluble, and a solvent from which both the glucosides and the aglicone would precipitate in a crystalline form which could be easily filtered and purified, ether has been found to be critically the only solvent which satisfies these many and different requirements.

Thus, while solvents such as acetone, ethyl acetate, chloroform, and aliphatic and aromatic hydrocarbons have a satisfactory solvent power towards the chlorophyll and fatty matter contained in the total ligule extract, they have practically no solvent power towards tannins, polyhydroxylated cumarin derivatives and like compounds, which thus remain with the apigenin and its glucosides as a strong impurity, which can certainly not be tolerated in a product for pharmaceutical use.

On the other hand, solvents such as alcohols and water which have a good solvent power towards all the foreign substances contained in the extract from stage (a) also dissolve the apigenin glucosides and therefore have no resolutive power. Finally, with regard to stage (c) for producing free apigenin, it has been found that if strong dilute acids with a concentration not exceeding 1% are used, then hydrolysis of the glucosides does not occur. If strong acids are used at a concentration of 1 to 10%, hydrolysis is very slow. With a strong acid of 10% concentration, the optimum hydrolysis rate is reached, and this does not further increase as the concentration increases. In fact, at high concentrations the apigenin becomes soluble, and there is a risk of partially decomposing the product.

Of the various acids, the preferred acid is obviously HCl both for economical reasons and because the danger of decomposition is reduced to a minimum.

As initially stated, the present invention also relates to the use of the pure product apigenin in human therapy.

In this respect, pharmacological studies carried out on apigenin have shown that it has good spasmolytic activity both on the intestinal and bronchial muscular systems, in addition to having good anti-inflammatory and anti-shock activity.

Its spasmolytic activity, which seems to be it main activity, lies between ½ and ¼ of the activity of papaverine. However, whereas papaverine has an LD50 i.v. of 25-30 mg/kg, apigenin shows an absolute lack of toxicity up to 250 mg/kg i.v.

This means that apigenin has a therapeutic index which is extremely more interesting than that of papaverine, and therefore its use in the pharmaceutical field in all cases in which up to the present time papaverine was the best medically available drug can give truly satisfactory results, under conditions of absolute safety for the patient.

Apigenin can be administered orally or parenterally by the normal forms of administration, such as capsules, tablets, oral suspensions and injectable suspensions.

In order to allow the process according to the present invention to be more easily reproduced, one detailed working example thereof is given hereinafter, but this can be varied within the range heretofore defined.

EXAMPLE (a)

50 grams of Bulgarian camomile ligules (1976 production, moisture content 8%) are extracted in a continuous extractor with a water/ethyl alcohol mixture containing 7 parts by volume of waer and 3 parts by volume of ethanol.

Extraction is carried out for 7 hours. To prevent the vegetable material becoming insufficiently wetted by the solvent and thus imperfectly extracted, the ligules are placed in cloth bags, in a quantity of not more than 6-7 grams per bag, and totally covered with the solvent.

(b)

The extract obtained is evaporated to dryness and then taken up in 500 ml of ether. The mixture is left under vigorous agitation for 24 hours at ambient temperature and is then filtered through a porous filter.

The filtered solid is washed with three 50 ml portions of ether, and then dried under vacuum at ambient temperature. 9 g of product are obtained in the form of a yellow powder.

(c)

The yellow powder obtained in the preceding stage is placed in a 1000 ml flask, into which 500 ml of 10% HCl is poured. The mixture is heated under reflux for about 10 hours.

After this time, it is filtered at a temperature of 50° C., the precipitate is washed on the filter until neutrality, and is then dried in an oven at 100° C. By crystallising from 96% ethanol, 2.61 g of very pure apigenin are obtained (characteristics corresponding to those of the literature), equal to a yield of 5.22% by weight with respect to the initial ligules.

What we claim is:

1. A process for preparing very pure apigenin for therapeutic use, wherein the ligules of Matricaria Chamomilla L. are extracted continuously for 7-8 hours with a water/ethanol mixture containing at least 30% by volume of ethanol; the extract is evaporated to dryness and taken up in a volume of ether in the ratio of about 10 parts by volume to 1 part by weight of the initial ligules, and is kept under strong agitation for about 24 hours at ambient temperature; the precipitated solid is hydrolysed with 10% HCl by heating under reflux for about 10 hours.

2. A process as claimed in claim 1, wherein the apigenin obtained is purified by crystallisation from ethanol.

* * * * *

UNITED STATES PATENT AND TRADEMARK OFFICE
CERTIFICATE OF CORRECTION

PATENT NO. : 4,313,880
DATED : February 2, 1982
INVENTOR(S) : Claudio Redaelli, Missaglia, Italy It is certified that error appears in the above—identified patent and that said Letters Patent is hereby corrected as shown below:

Abstract and Title Page

Under Item [73] Assignee:

Cancel "Benomelli" and substitute --Bonomelli--

Signed and Sealed this

Fourteenth Day of December 1982

[SEAL]

Attest:

GERALD J. MOSSINGHOFF

Attesting Officer — Commissioner of Patents and Trademarks